United States Patent
Matsuda (10) Patent No.: US 11,311,180 B2
(45) Date of Patent: Apr. 26, 2022

(54) ENDOSCOPE CONFIGURED TO CHANGE A LENGTH OF A BENDABLE PART

(71) Applicant: Olympus Corporation, Hachioji (JP)

(72) Inventor: Eiji Matsuda, Sagamihara (JP)

(73) Assignee: OLYMPUS CORPORATION, Tokyo (JP)

(*) Notice: Subject to any disclaimer, the term of this patent is extended or adjusted under 35 U.S.C. 154(b) by 580 days.

(21) Appl. No.: 16/171,529

(22) Filed: Oct. 26, 2018

(65) Prior Publication Data

US 2019/0059700 A1 Feb. 28, 2019

Related U.S. Application Data

(63) Continuation of application No. PCT/JP2017/015530, filed on Apr. 18, 2017.

(30) Foreign Application Priority Data

Aug. 19, 2016 (JP) .............................. JP2016-161214

(51) Int. Cl.
*A61B 1/005* (2006.01)
*A61B 1/00* (2006.01)

(52) U.S. Cl.
CPC .......... *A61B 1/0057* (2013.01); *A61B 1/0052* (2013.01); *A61B 1/0055* (2013.01); *A61B 1/00078* (2013.01)

(58) Field of Classification Search
CPC . A61B 1/0057; A61B 1/00078; A61B 1/0052; A61B 1/0055
See application file for complete search history.

(56) References Cited

U.S. PATENT DOCUMENTS

2001/0052721 A1* 12/2001 Tanaka ...................... A61B 8/12
297/367 R
2002/0017515 A1* 2/2002 Obata .................. A61B 1/0055
219/137 R (Continued)

FOREIGN PATENT DOCUMENTS

JP 2003-038421 2/2003
JP 2005-160790 6/2005

(Continued)

OTHER PUBLICATIONS

International Search Report and Written Opinion from corresponding International Application No. PCT/JP2017/015530, dated Jul. 4, 2017.

*Primary Examiner* — Aaron B Fairchild
*Assistant Examiner* — Shankar Raj Ghimire
(74) *Attorney, Agent, or Firm* — Oliff PLC (57) ABSTRACT

An endoscope includes a bendable part having a first bendable portion, a second bendable portion, a flexible tube part, and an operation unit. An upward coil is attached at its distal end on the second bendable portion. A second coil is attached at its distal end on the flexible tube part and at its proximal end in the operation unit. An upward coil receiver is disposed in the operation unit with the upward coil being connected to the upward coil receiver. A selection member presses the upward coil receiver and compresses the upward coil. A bent length selection wire is connected to the selection member. A selection pulley is disposed in the operation unit and is configured to allow the upward coil receiver to advance or retract via the selection member. A cam plate having cam portions is formed to increase a frictional force with rotation of the selection pulley.

9 Claims, 9 Drawing Sheets

(56) References Cited

U.S. PATENT DOCUMENTS

| | | | | |
|---|---|---|---|---|
| 2007/0043261 A1* | 2/2007 | Watanabe | A61B 1/00078 | 600/144 |
| 2008/0214897 A1* | 9/2008 | Matsuo | A61B 1/0055 | 600/139 |
| 2009/0099420 A1* | 4/2009 | Woodley | A61B 1/0053 | 600/142 |
| 2010/0168519 A1* | 7/2010 | Matsuo | A61B 1/0055 | 600/139 |
| 2011/0282153 A1* | 11/2011 | Ueki | A61B 1/0052 | 600/149 |
| 2012/0065628 A1* | 3/2012 | Naito | A61B 1/0057 | 606/1 |
| 2013/0012781 A1* | 1/2013 | Kaneko | A61B 1/0057 | 600/148 |
| 2013/0096384 A1* | 4/2013 | Arai | A61B 1/0055 | 600/144 |
| 2013/0178705 A1* | 7/2013 | Takeuchi | A61B 1/0052 | 600/144 |
| 2014/0118515 A1* | 5/2014 | Lee | A61B 1/0055 | 348/65 |
| 2014/0135576 A1* | 5/2014 | Hebert | A61B 1/0055 | 600/109 |
| 2015/0087910 A1* | 3/2015 | Okazaki | A61B 1/0057 | 600/146 |
| 2015/0313447 A1* | 11/2015 | Arai | A61B 1/0055 | 600/146 |
| 2016/0150945 A1* | 6/2016 | Okamoto | A61B 1/31 | 600/114 |
| 2016/0353974 A1* | 12/2016 | Kakehashi | A61B 1/0057 | |
| 2020/0046213 A1* | 2/2020 | Bendory | A61B 1/0669 | |

FOREIGN PATENT DOCUMENTS

| | | |
|---|---|---|
| JP | 2007-282693 | 11/2007 |
| JP | 4856289 | 11/2011 |
| JP | 2012-231884 | 11/2012 |
| JP | 2016-054967 | 4/2016 |
| WO | 2015029718 | 3/2015 |
| WO | 2017043124 | 3/2017 |

* cited by examiner

ENDOSCOPE CONFIGURED TO CHANGE A LENGTH OF A BENDABLE PART

CROSS-REFERENCE TO RELATED APPLICATIONS

This application is a continuation application of PCT Application No. PCT/JP2017/015530 filed on Apr. 18, 2017, which in turn claim priority to the Japanese Patent Application No. 2016-161214 filed on Aug. 19, 2016 in Japan which is hereby incorporated by reference in its entirety.

TECHNICAL FIELD

The technology disclosed herein relates to an endoscope having a bendable part in an insert section.

DESCRIPTION OF THE RELATED ART

In recent years, endoscopes are used with objects or subjects under examination or treatment in the medical and industrial fields. An endoscope for use in the medical field is configured to enable a user to observe an organ or various treatments by inserting a slender insert section into a subject under examination or treatment.

Known endoscopes include those which have a bendable part to permit changing the direction of an observation visual field in a desired direction as disclosed in Japanese Patent JP 2007-282693A. Disclosed in Japanese Patent JP 2007-282693A is a technology that has made it possible to adjust the attaching position of a guide coil in an operation unit. An operation wire is inserted in the guide coil to perform bending operation of the bendable part.

In general, the bendable part of a conventional endoscope has a characteristic that upon bending operation, the bendable part is bent over its length forward of its proximal end. With an endoscope having such a characteristic, a problem arises that being in a small radius is not readily possible.

Therefore, there is a need for an endoscope that has a superior operability and enable a user to overcome the aforementioned drawbacks.

BRIEF SUMMARY OF EMBODIMENTS

The disclosed technology is directed to an endoscope includes a bendable part having a first bendable portion and a second bendable portion formed on a distal end thereof and is configured to be bendable by pulling or relaxing a bending operation wire. A flexible tube part is disposed consecutively on a proximal end of the second bendable portion. An operation unit is disposed consecutively on a proximal end of the flexible tube part.

A first guide coil includes a distal end attached on a distal end of the second bendable portion and having the bending operation wire internally inserted therethrough. A second guide coil includes a distal end and a proximal end in which the distal end of the second guide coil is attached to a distal end portion of the flexible tube and the proximal end of the second guide coil is attached in the operation unit. The first guide coil is internally inserted into second guide coil.

A movable member is disposed advanceable and retractable in the operation unit with the first guide coil being connected at a proximal end thereof to the movable member.

A selection member is configured to be moved to press the movable member and to compress the first guide coil, whereby the first guide coil is increased in stiffness to change the bendable part from a long-length bent state. The bendable part is bent over its entirety to a short-length bent state and in which the first bendable portion is bent.

A selector lever braking mechanism is configured to maintain the short-length bent state to which the bendable part is changed by pressing the movable member via the selection member.

A transmission member having a distal end that is connected to the selection member and is configured to bring the selection member into contact with the movable member so that a force is transmitted to push in the movable member.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

One of the problems with prior endoscopes have been that bending in a small radius is not possible. Thus, insertion maneuverability is lowered upon inserting an insert section toward a deep part of a complex body cavity. Therefore, the observation, treatment or the like of a part of the subject under examination, treatment or the like can be hardly conducted. The technology disclosed herein has one aspect thereof the provision of an endoscope of excellent operability that (i) ensures improved insertion maneuverability into a deep part of a complex body cavity by changing a bendable part between a "long-length bent state" and a "short-length bent state" and (ii) enables observation or treatment while maintaining the short-length bent state.

An endoscope according to another aspect of the technology disclosed herein includes a bendable part, a flexible tube part, an operation unit, a first guide coil, a second guide coil, a movable member, a selection member, a transmission member, a rotatable member, and a plate member. The bendable part includes a first bendable portion and a second bendable portion arranged in this order from a distal end of the bendable part. The bendable part is configured to be bent by pulling or relaxing a bending operation wire. The flexible tube part is disposed consecutively on a proximal end of the second bendable portion. The operation unit is disposed consecutively on a proximal end of the flexible tube part. The first guide coil is attached at a distal end thereof on a distal end portion of the second bendable portion. The first guide coil includes the bending operation wire internally inserted therethrough. The second guide coil is attached at a distal end thereof on a distal end portion of the flexible tube part. The second guide coil is attached at a proximal end thereof in the operation unit. The second guide coil includes the first guide coil internally inserted therethrough. The movable member is disposed advanceable and retractable in the operation unit. The first guide coil is connected at a proximal end thereof to the movable member. The selection member is configured to be moved (i) to press the movable member and (ii) to compress the first guide coil. When the first guide coil is compressed, the first guide coil is increased in stiffness to change the bendable part from a long-length bent state to a short-length bent state. In the long-length bent state, the bendable part is bent over its entirety. In the short-length bent state, only the first bendable portion is bent. The transmission member is connected on a side of a distal end thereof to the selection member. The transmission member is configured to bring the selection member into contact with the movable member so that a force is transmitted to push in the movable member. The rotatable member is rotatably disposed in the operation unit. The transmission member is connected on a side of its proximal end to a position of a predetermined rotation radius on the rotatable member. The transmission member is configured to rotate so that the transmission member is pushed or pulled to allow the movable member to advance or retract via the selection member. The plate member is disposed slidably side by side with the rotatable member in the operation unit. The plate includes a first raised portion formed so that a sliding friction force increased with rotation of the rotatable member.

It is to be noted that the drawings relating to an embodiment are schematic. The relationship between the thickness and width of each portion, part or section, the ratio in thickness of individual portions, parts and section, and the like are different from the actual ones. In the drawings, portions, parts and section may be illustrated in different dimensional relationships or at different dimensional ratios.

Figure 1:
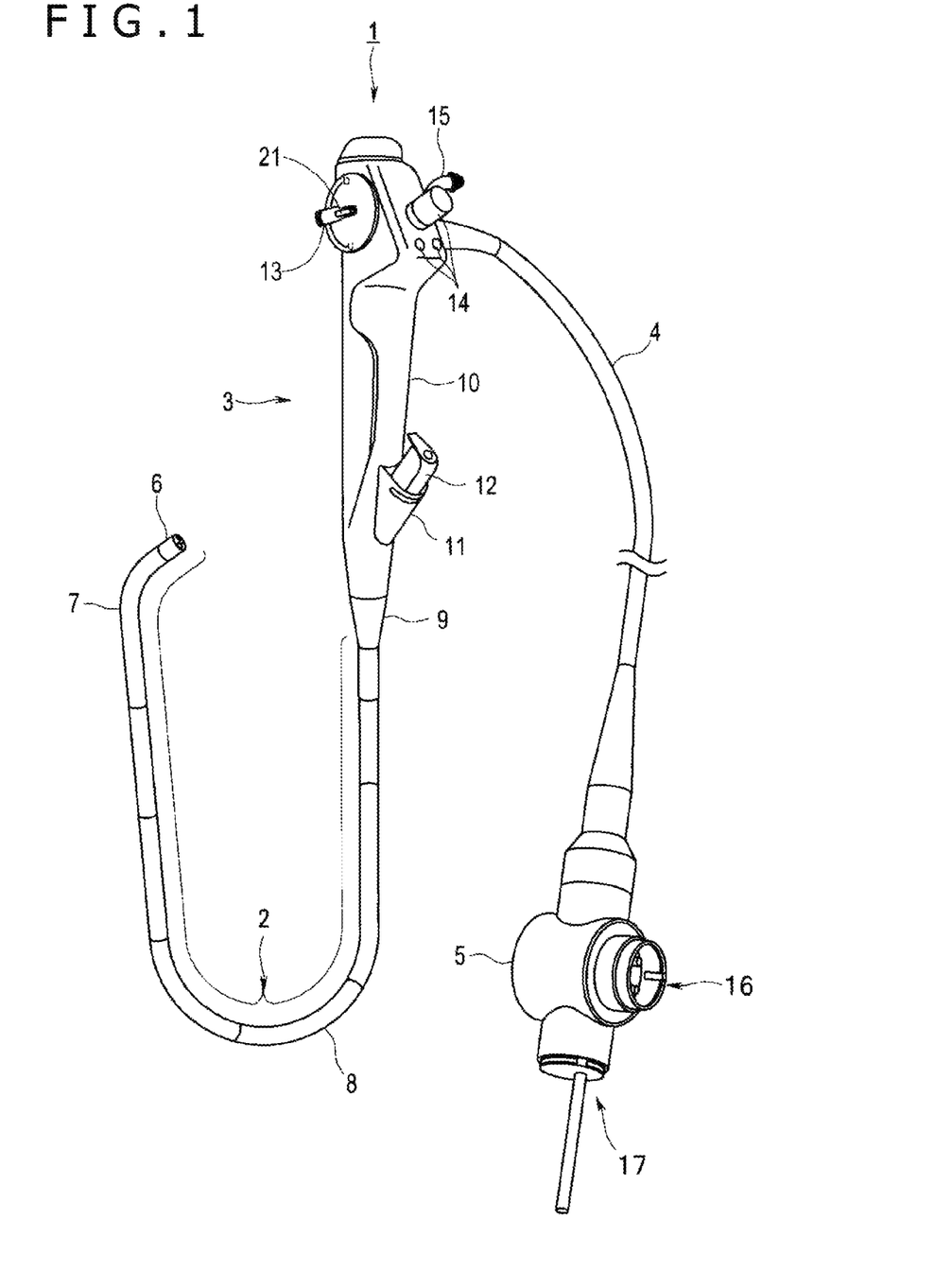
FIG. 1 is a general view illustrating an endoscope according to the technology disclosed herein.

As illustrated in FIG. 1, an electronic endoscope, hereinafter simply called "the endoscope," 1 according to this embodiment is illustrated as a bronchial endoscope by way of example. It is to be noted that the endoscope 1 is not limited to such bronchial endoscope but may be a so-called upper endoscope or a so-called lower endoscope. The upper endoscope is introduced from an oral cavity or mouth and is guided into the stomach, the duodenum or the like. The lower endoscope is introduced from the anus and is guided into the colon and rectum. The endoscope 1 is primarily configured by an insert section 2, an operation unit 3, and a universal cord 4. The insert section 2 is formed in the shape of a slender tube. The operation unit 3 is disposed consecutively on a proximal end of the insert section 2. The universal cord 4 is an endoscope cable, and is disposed extending from the operation unit 3. On an end portion of the universal cord 4, an endoscope connector 5 is disposed. The insert section 2 is a tubular member and has flexibility. The insert section 2 is formed of a tip portion 6, a bendable part 7 and a flexible tube part 8 all of which are attached to one another from the side of a distal end of the insert section 2. Generally, at the tip portion 6, an observation window, an illumination window and a surgical instrument channel opening can be installed, even though they are not illustrated in FIG. 1. Furthermore, an imaging unit and/or an illuminating optical system may be built in the tip portion 6. The imaging unit has a CCD sensor or CMOS sensor which is an imaging device having imaging means therein. The illuminating optical system radiates illuminating light, which is transmitted from unillustrated light transmission means, onto a subject under examination or treatment.

The endoscope 1 is, however, not limited to an electronic endoscope, but may be a so-called fiber scope with an image guide fiber arranged in the insert section 2. The bendable part 7 is configured to be actively bendable in two directions of up and down by turning operation of a bending operation lever 13 disposed in the operation unit 3 as a bending operation member to be described hereinafter. The bendable part 7 is, however, not limited to the configuration that it is bendable in the two directions of up and down, but may have a configuration that it is bendable in four directions including left-right directions in addition to the up-down directions, that is, in the entire circumferential direction of UP-DOWN/RIGHT-LEFT about its central axis by upward, downward, leftward and rightward operations. The flexible tube part 8 is a tubular member formed with bendability so that it is passively bendable. Built-in endoscope components are contained inside the flexible tube part 8. These built-in endoscope components include, in addition to an unillustrated surgical instrument channel, various signal lines a light guide, and the like. The various signal lines extends from the imaging unit. The light guide projects illuminating light from a light source device and allows it to radiate from the tip portion 6.

The operation unit 3 has a grip handle 10, operation buttons 14, and a suction valve 15. The grip handle 10 is disposed consecutively with the flexible tube part 8 via a snap preventing portion 9. The grip handle 10 is held by hand when a user operates the endoscope 1. The flexible tube part 8 is covered at a proximal end thereof by the snap preventing portion 9. The operation buttons 14 are arranged to control various endoscopic functions. The operation unit 3 includes a surgical instrument insertion part 11 having a port through which unillustrated various surgical instruments are to be inserted. The surgical instrument insertion part 11 is in communication with the surgical instrument insertion channel. The surgical instrument insertion channel also is used as a suction line, via a branch member inside the operation unit 3. A forceps plug 12 is a lid member for openably closing the surgical instrument insertion port. The forceps plug 12 can be attached to and detached from the surgical instrument insertion part 11, and therefore can be replaced with various surgical instruments. Further, a selector lever 21 is disposed in the vicinity of a basal end of the bending operation lever 13. The selector lever 21 is used as a bent length selection lever or a selection operating member. The selector lever 21 is operated upon changing the bendable part 7 to a "long-length bent state" or "short-length bent state". Regarding a bent length selection mechanism including the selector lever 21, a detailed description is described hereinafter.

The universal cord 4 is a composite cable that contains various signal lines, the light guide and the like. The various signal lines (i) extend from the tip portion 6, (ii) are inserted inside the insert section 2, (iii) reach the operation unit 3, and then (iv) pass through the operation unit 3. The light guide transmits illuminating light from the unillustrated light source device. The endoscope connector 5 has an electric connector adapter 16 on a side wall thereof, and also has a light source connector adapter 17. A connector is attached to the electric connector adapter 16 and is arranged on a signal cable. The signal cable is attached to an unillustrated video processor as an external device. The light source connector adapter 17 is attached to the light source device as an external device.

Figure 2:
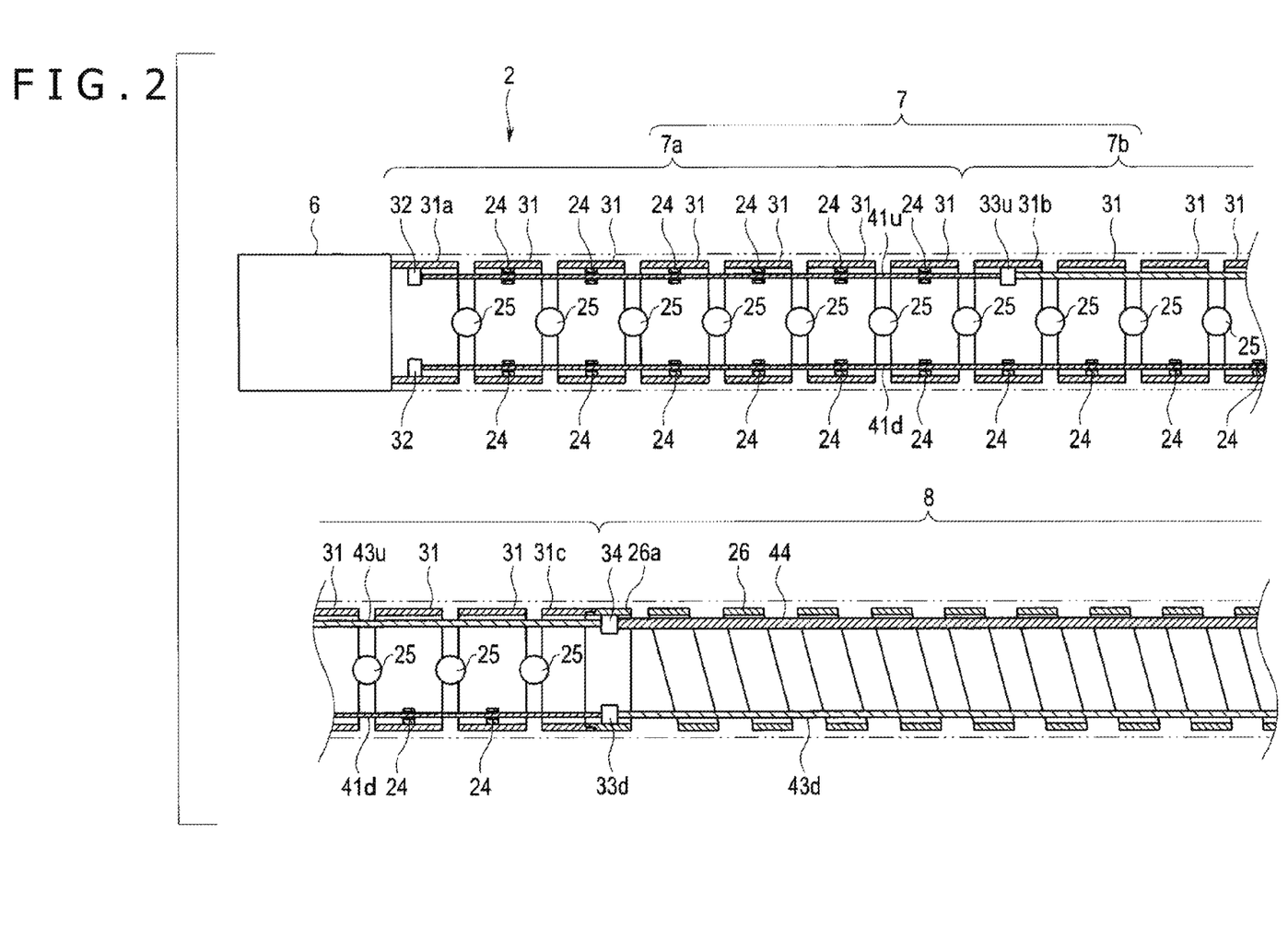
FIG. 2 is a view illustrating a configuration in an insert section, primarily the configuration of a bendable part as depicted in FIG. 1.

With reference to FIG. 2, a description will be made regarding the insert section 2, especially the bendable part 7. As illustrated in FIG. 2, the bendable part 7 includes a plurality of ring-shaped bending elements 31. The individual bending elements 31 are pivotally connected to one another by rivets 25. The plurality of bending elements 31 are covered at outer circumferences thereof with a braid as a braided tube and a bendable rubber although neither the braid nor the bendable rubber is illustrated. The bendable part 7 in this embodiment includes a first bendable portion 7a and a second bendable portion 7b. The first bendable portion 7a is disposed on the side of the tip portion 6. The second bendable portion 7b is disposed on the side of the flexible tube part 8. The first bendable portion 7a makes up from a most distal bending element 31a to before an intermediate bending element 31b. The most distal bending element 31a is connected to the tip portion 6. The intermediate bending element 31b is disposed at a midway position of the insert section 2. The second bendable portion 7b makes up from the intermediate bending element 31b to a most proximal bending element 31c. It is to be noted that concerning the first bendable portion 7a and second bendable portion 7b, the numbers of the bendable elements, kinds and the like of the bending elements 31 can be suitably set according to the purpose of use of the endoscope 1 in each biological lumen into which the bendable part 7 is to be inserted. On the most distal bending element 31a, two wire anchors 32 are disposed at opposite positions substantially symmetrical to each other with respect to a center point. On the two wire anchors 32, an "upward bending operation wire" 41u and a "downward bending operation wire" 41d are attached at respective each distal ends thereof. The upward bending operation wire 41u and downward bending operation wire 41d pass inside the insert section 2. The upward bending operation wire 41u and downward bending operation wire 41d are contained into the operation unit 3. The upward bending operation wire 41u and downward bending operation wire 41d are disposed through corresponding wire guides 24 arranged on the individual bending elements 31 in the first bendable portion 7a.

The intermediate bending element 31b is at a distal end position of the second bendable portion 7b. A first guide coil anchor 33 is arranged in the intermediate bending element 31b. The first guide coil anchor 33 is constructed on the side of the upward bending operation wire 41u. The first guide coil anchor 33 is an upward guide coil anchor 33u. A first guide coil 43 (FIG. 4A) includes an upward guide coil 43u and a downward guide coil 43d. The upward guide coil 43u is attached at a distal end thereof on the coil anchor 33u. The most proximal bending element 31c is disposed at a proximal end position of the second bendable portion 7b. The most proximal bending elements 31c is attached to a connection pipe 26a to the bendable part 7. The connection pipe 26a is located at a distal end of a helical tube 26 disposed in the flexible tube part 8. The connection pipe 26a includes a second guide coil anchor 34 disposed on the side of the upward bending operation wire 41u. A downward guide coil anchor 33d as the other first guide coil anchor 33 is disposed on the side of the downward bending operation wire 41d. The second guide coil anchor 34 and the downward guide coil anchor 33d are disposed at opposite positions substantially symmetrical to one another with respect to a center point. A second guide coil 44 includes a distal end attached to the second guide coil anchor 34. On the downward guide coil anchor 33d, the downward guide coil 43d as the other one of the first guide coils 43 is attached at a distal end thereof.

The upward guide coil 43u and downward guide coil 43d are small-diameter metal coils. These respective guide coils 43u and 43d pass inside the insert section 2 and are contained within the operation unit 3. The upward bending operation wire 41u is inserted inside the upward guide coil 43u, while the downward bending operation wire 41d is inserted inside the downward guide coil 43d. The second guide coil 44 is a large-diameter metal coil, and has an inner diameter greater than the outer diameter of the upward guide coil 43u. The upward guide coil 43u is inserted through the second guide coil 44. The upward bending operation wire 41u is inserted in the upward guide coil 43u. Described specifically, in the insert section 2 in this embodiment, a wire to wire structure is formed inside the first bendable portion 7a. In the wire to wire structure, the upward bending operation wire 41u and downward bending operation wire 41d are disposed. Inside the second bendable portion 7b, on the other hand, a wire to coil structure and a single wire structure are formed. In the wire to coil structure, the upward bending operation wire 41u is inserted in the upward guide coil 43u. In the single wire structure, the downward bending operation wire 41d is disposed. Inside the flexible tube part 8, a wire to double coil structure and a wire to coil structure are formed. In the wire to double coil structure, the upward guide coil 43u with the upward bending operation wire 41u inserted therein is inserted in the second guide coil 44. In the wire to coil structure, the downward bending operation wire 41d is inserted in the downward guide coil 43d.

Figure 3:
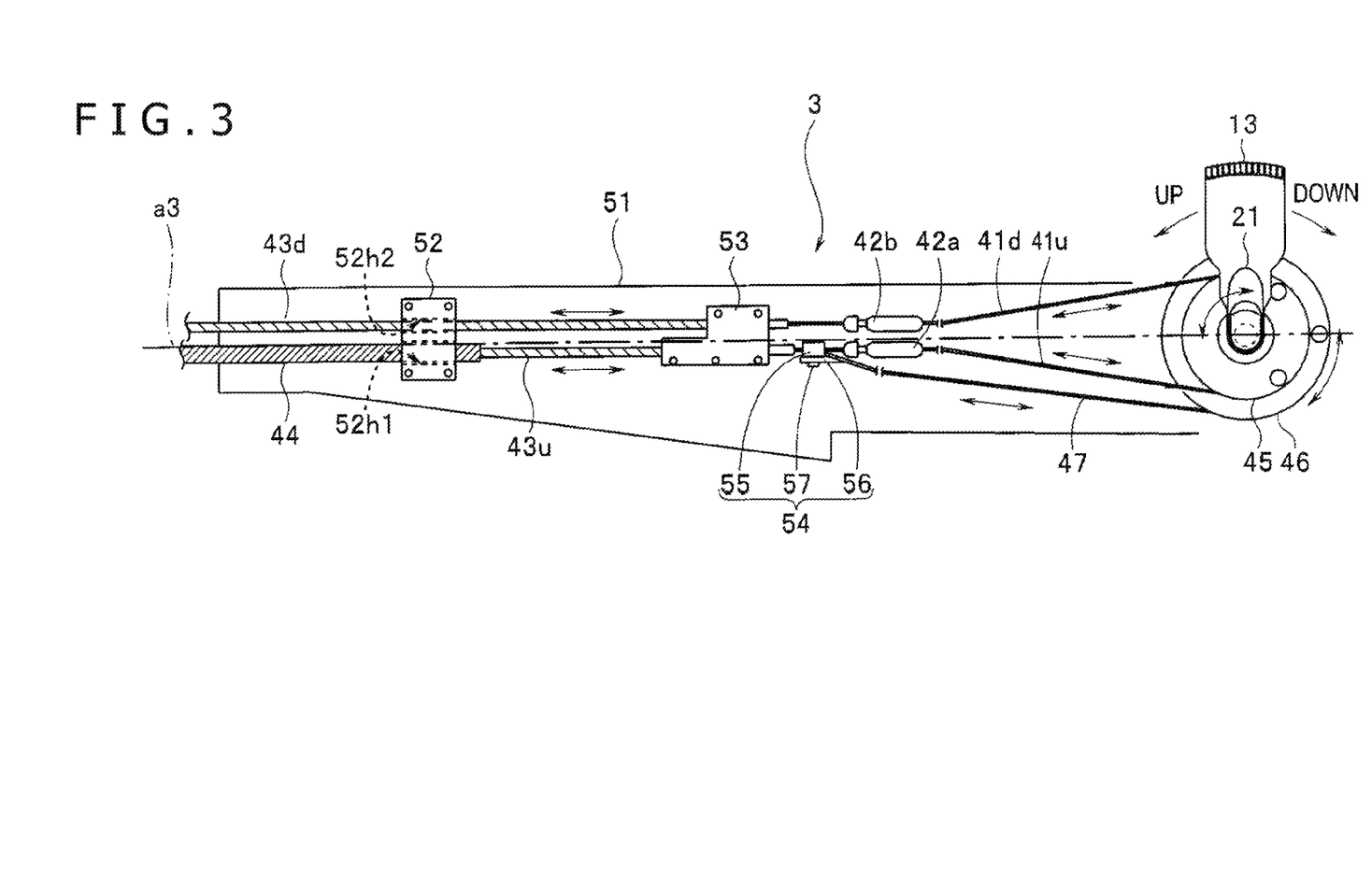
FIG. 3 is a view illustrating a configuration in an operation unit as depicted in FIG. 1.

With reference to FIG. 3, a description will be made of the schematic configuration in the operation unit 3. As illustrated in FIG. 3, a frame 51 is disposed in the operation unit 3. The frame 51 is made, for example, of a metal having rigidity such as aluminum or stainless steel. On the side of a proximal end of the frame 51, a bending operation pulley 45 and a bent length selection pulley 46 are rotatably disposed. The bending operation pulley 45 rotates in conjunction with turning operation of the bending operation lever 13. To predetermined positions on an outer circumferential wall of the bending operation pulley 45, the upward bending operation wire 41u and downward bending operation wire 41d are connected at each proximal ends thereof. The upward bending operation wire 41u and downward bending operation wire 41d are pulled or relaxed relative to one another by rotation of the bending operation pulley 45. Further, turn buckles 42a and 42b are interposed in the upward bending operation wire 41u and downward bending operation wire 41d for the adjustment of their lengths, respectively.

According to this endoscope 1, the bendable part 7 is bent in the up-down direction by turning operation of the bending operation lever 13. The amount of bending, or bending angle, of the bendable part 7 in the up-down direction is determined based on the relative pull or relax amounts of the upward bending operation wire 41u and downward bending operation wire 41d. As the mechanism that bends the bendable part 7 by the bending operation lever 13 as described hereinbefore is similar to the conventional configuration, any further detailed description is omitted to avoid redundancy. An anchor block 52 is attached by unillustrated screws or the like on the side of a distal end of the frame 51. The anchor block 52 has an anchor hole 52h1 and a wire insertion hole 52h2. The second guide coil 44 is attached at a proximal end portion thereof in the anchor hole 52h1. In the anchor hole 52h1, the second guide coil 44 is attached at the proximal end portion thereof, and in the wire insertion hole 52h2, the downward guide coil 43d is inserted. The upward guide coil 43u extends from the side of the proximal end of the second guide coil 44 attached on the anchor block 52. Numeral 53 designates a first guide coil attachment block, which is attached by unillustrated screws or the like at a predetermined position on a midway part of the frame 51. On the first guide coil attachment block 53, an upward guide coil receiving member 61 and a downward guide coil receiving member 71 are disposed and both of which is described hereinafter. Numeral 54 designates a selection device, which has a selection member 55, a fixing plate 56, and a support pin 57. The selection device 54 is disposed at a predetermined position in the vicinity of the first guide coil attachment block 53.

The bent length selection pulley 46 is a rotatable member, which rotates in conjunction with turning operation of the selector lever 21. To a predetermined position on an outer circumferential wall of the bent length selection pulley 46, a bent length selection wire 47 is connected on the side of one end thereof, specifically a proximal end thereof. The bent length selection wire 47 is configured to be pulled by rotation of the bent length selection pulley 46 in an UP direction from an initial position in the figure. The bent length selection wire 47 is connected to the selection member 55, on the side of the other end thereof, specifically a distal end thereof.

Figure 4A:
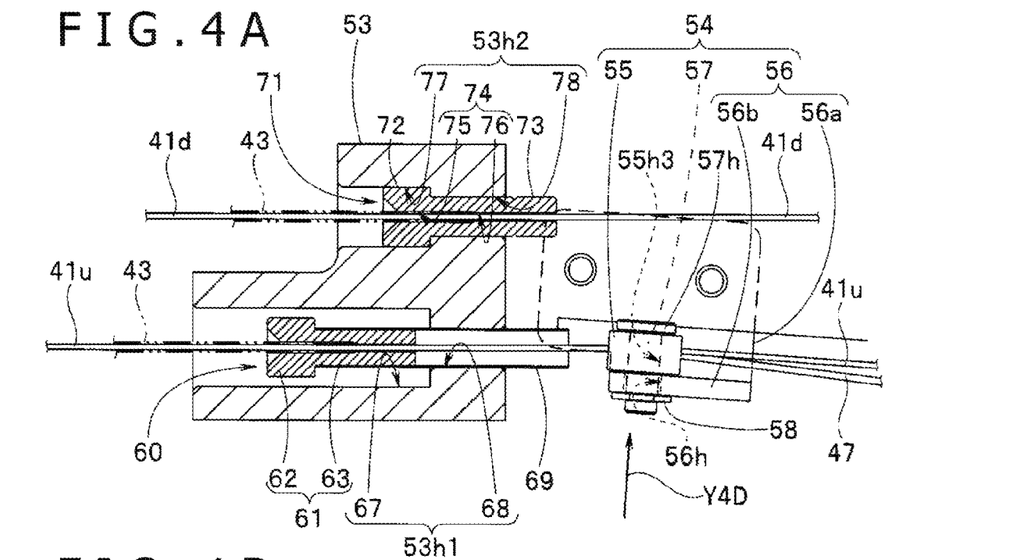
FIG. 4A is a view illustrating a first guide coil attachment block and a selection device.

Now referring to FIG. 4A to FIG. 4F, the configuration and operation of the first guide coil attachment block 53 and selection device 54 is described. First, with reference to FIG. 4A and FIG. 4B, the first guide coil attachment block 53 is described. As illustrated in FIG. 4A, the first guide coil attachment block 53 includes a first stepped hole 53h1 and a second stepped hole 53h2, both of which are formed in parallel to a longitudinal axis of the operation unit, as noted at sign a3 in FIG. 3. In this embodiment, an upward guide coil receiver 60 is a movable member. The upward guide coil receiver 60 is disposed advanceable and retractable in the first stepped hole 53h1. The downward guide coil receiving member 71 is disposed advanceable and retractable in the second stepped hole 53h2. The downward guide coil receiving member 71 is a stepped pin, and has a large-diameter portion 72 and a small-diameter portion 73. A stepped hole 74 is a through-hole. The stepped hole 74 is centrally formed through the downward guide coil receiving member 71. The stepped hole 74 has a large-diameter coil hole 75 and a small-diameter wire insertion hole 76. The stepped hole 74 has an opening through a bottom wall of the coil hole 75 so that the wire insertion hole 76 is in communication with the outside and the internal space of the coil hole 75. The downward guide coil 43d is attachably disposed at a proximal end portion thereof in the coil hole 75. In the wire insertion hole 76, the downward bending operation wire 41d is inserted. The downward bending operation wire 41d is led out of the downward guide coil 43d. The downward bending operation wire 41d passes through the wire insertion hole 76 and then extends to the outside.

Figure 4B:
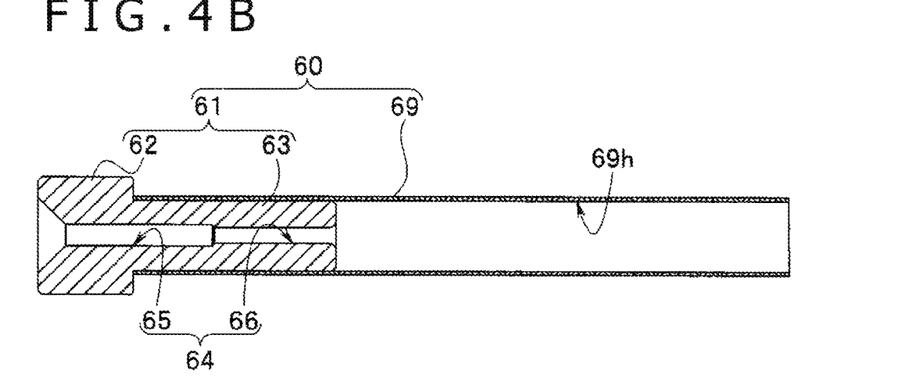
FIG. 4B is a view illustrating a guide coil receiving member.

As illustrated in FIG. 4A, the second stepped hole 53h2 has a large-diameter hole 77 and a small-diameter hole 78. The downward guide coil receiving member 71 is disposed in the second stepped hole 53h2, with the small-diameter portion 73 and large-diameter portion 72 being inserted in the small-diameter hole 78 and large-diameter hole 77, respectively. On the other hand, as illustrated in FIG. 4B, the upward guide coil receiver 60 is configured, of the upward guide coil receiving member 61 and a pipe 69. The upward guide coil receiving member 61 is configured substantially the same as the downward guide coil receiving member 71. The pipe 69 has a through-hole 69h. The upward guide coil receiving member 61 has a large-diameter portion 62 and a small-diameter portion 63. On the small-diameter portion 63, the pipe 69 is externally fitted at a distal end portion thereof. The pipe 69 is attached, for example, with an adhesive on the small-diameter portion 63. The pipe 69 extends at a proximal end portion thereof to the outside from the side of a proximal end face of the first guide coil attachment block 53 as illustrated in FIG. 4A. A stepped hole 64 is a through-hole and is centrally formed through the upward guide coil receiving member 61. The stepped hole 64 has a large-diameter coil hole 65 and a small-diameter wire insertion hole 66. The stepped hole 64 has an opening through a bottom wall of the coil hole 65, so that the wire insertion hole 66 is in communication with the outside and the internal space of the coil hole 65. The upward guide coil 43u is attachably disposed at a proximal end portion thereof in the coil hole 65. In the wire insertion hole 66, the upward bending operation wire 41u is inserted. The upward bending operation wire 41u is led out of the upward guide coil 43u. The upward bending operation wire 41u is led out from the inside of the wire insertion hole 65. The upward bending operation wire 41u passes in the through-hole 69h of the pipe 69 and then extends to the outside.

As illustrated in FIG. 4A, the first stepped hole 53h1 has a large-diameter hole 67 and a small-diameter hole 68. The pipe 69 makes up the upward guide coil receiver 60. The pipe 69 is slidably disposed at a proximal end portion thereof in a predetermined fitted relationship in the small-diameter hole 68 of the first stepped hole 53h1. The large-diameter portion 62 of the upward guide coil receiver 60 is disposed in a loose fit state in the large-diameter hole 67 of the first stepped hole 53h1. Next, the selection device 54 will be described with reference to FIG. 4A, FIG. 4C and FIG. 4D. The selection member 55 as illustrated in FIG. 4A is turnably supported by the support pin 57 on the fixing plate 56.

Figure 4C:
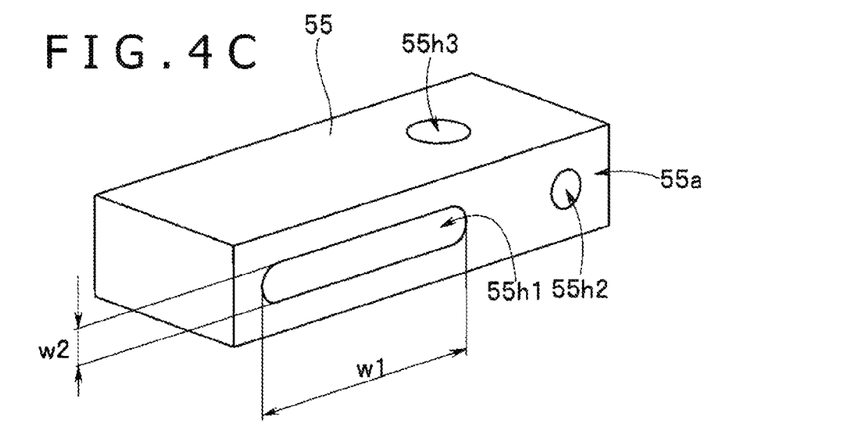
FIG. 4C is a view illustrating a selection member.

As illustrated in FIG. 4C, the selection member 55 is a pressing block in the shape of a rectangular parallelepiped.

The selection member 55 includes a slot 55h1, a wire anchor hole 55h2 and a pin bore 55h3 formed at respective predetermined positions. In this embodiment, the slot 55h1 and wire anchor hole 55h2 have openings in a longitudinal side wall 55a. The slot 55h1 is a wire clearance slot, and the upward bending operation wire 41u is inserted in a loose fit state in the slot 55h1. The opening of the slot 55h1 has a flattened shape, its longer width w1 is set greater than the diameter of the upward bending operation wire 41u, and its shorter width w2 is set slightly greater than the diameter of the upward bending operation wire 41u. As a consequence, the inner wall of the slot 55h1 is prevented from coming into contact with the upward bending operation wire 41u when the selection member 55 is turned.

Figure 4D:
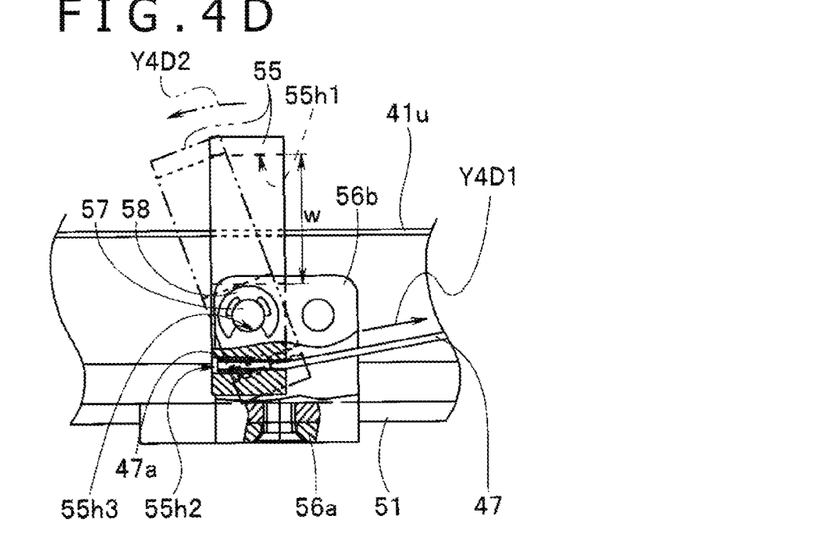
FIG. 4D is a view of the selection device as seen in a direction of arrow Y4D in FIG. 4A, in which a selection member has turned in association with pulling of a bent length selection wire.

As illustrated in FIG. 4D, the other end portion of the bent length selection wire 47 is disposed in the wire anchor hole 55h2. Numeral reference 47a designates a wire anchor block, and is a metal pipe that is disposed on and joined or attached integrally with the other end of the bent length selection wire 47. The wire anchor block 47a is integrally disposed on the other end of the bent length selection wire 47 and is integrally attached in the wire anchor hole 55h2, for example, by bonding. The pin bore 55h3 is disposed between the slot 55h1 and the wire anchor hole 55h2. The central axis of the pin bore 55h3 has a positional relationship orthogonal to the central axis of the slot 55h1 and the central axis of the wire anchor hole 55h2. The support pin 57 is inserted through the pin bore 55h3.

As illustrated in FIG. 4A and FIG. 4D, the fixing plate 56 is an L-shaped configuration, and includes a frame-side wall 56a and a selection-member-side wall 56b. The frame-side wall 56a is disposed on the frame 51. The selection member 55 is disposed on the selection-member-side wall 56b. The selection-member-side wall 56b includes a clearance hole, see at numeral reference 56h in FIG. 4A. The support pin 57 is inserted through the clearance hole 56h. As illustrated in FIG. 3, the fixing plate 56 is attached at a predetermined position on the frame 51 by unillustrated screws or the like.

Figure 4E:
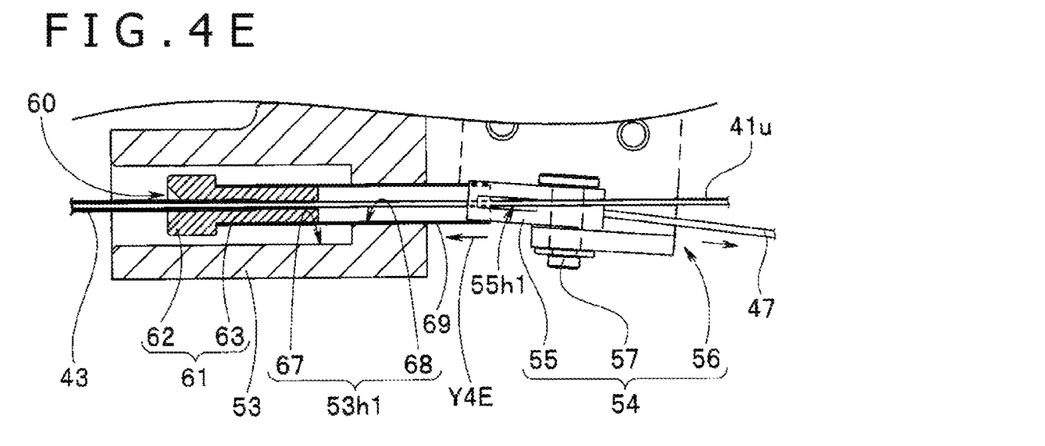
FIG. 4E is a view illustrating a state in which the selection member has come to contact with an end face of a pipe.

As illustrate in FIG. 4A, the selection member 55 is disposed on a mounting surface of the selection-member-side wall 56b of the fixing plate 56. In this disposed state, the support pin 57 is passed through the pin bore 55h3 of the selection member 55 and is inserted into the clearance hole 56h of the selection-member-side wall 56b. Then, the support pin 57 projects at a free end portion thereof over a predetermined length from the clearance hole 56h. This projecting free end portion has an unillustrated circumferential groove. An E-ring 58 is fitted in the groove as illustrated in FIG. 4A and FIG. 4D. Subsequently, the selection member 55 is turnably disposed by the support pin 57 on the fixing plate 56. Numeral reference 57h is a pin head portion, which has an outer diameter greater than that of the support pin 57. In association with pulling of the bent length selection wire 47 in a direction indicated by arrow Y4D1 in FIG. 4D, the selection member 55 turns about the support pin 57 in a direction indicated by arrow Y4D2 as indicated by a two-dot chain line. Then, as illustrated in FIG. 4E, the selection member 55 which has been turned under a pulling force by the bent length selection wire 47 comes into contact with an end face of the pipe 69 that outwardly extends from the proximal end face of the first guide coil attachment block 53.

Figure 4F:
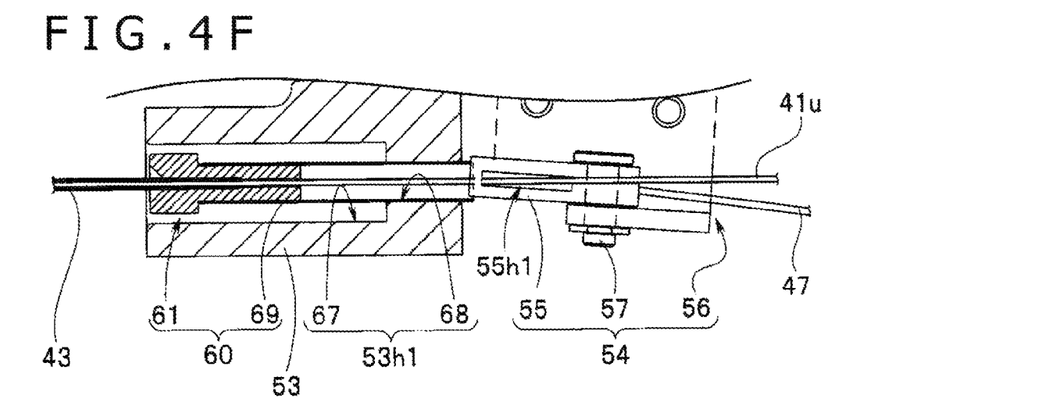
FIG. 4F is a view illustrating a state in which the pipe has been pressed in by the selection member to compress a first guide coil.

Subsequently, as the bent length selection wire 47 is pulled further, a pressing force is gradually transmitted from the selection member 55 to the pipe 69 so that the pipe 69 is progressively pushed in a direction indicated by arrow Y4E. As illustrated in FIG. 4F, the pipe 69 is moved toward its distal end by the turning movement of the selection member 55. In other words, the bent length selection wire 47 is used as a transmission member that when being pulled, transmits a pressing force from the selection member 55 to the pipe 69. As a consequence, the upward guide coil 43u with the upward bending operation wire 41u inserted therein is pushed in toward the distal end thereof. Therefore, the upward guide coil 43u is compressed to have increased stiffness. As illustrated in FIG. 2, the upward guide coil 43u is attached at the distal end thereof on the first guide coil anchor 33 disposed on the intermediate bending element 31b in the second bendable portion 7b. Therefore, the upward guide coil 43u progressively stiffens with compression. If the selector lever 21 is allowed to return to the initial state of FIG. 3, the bent length selection wire 47 is progressively relaxed. Then, the pipe 69 receives an elongating force from the upward guide coil 43u which has been compressed. The pipe 69 is allowed to progressively return to the original state that the pipe 69 extends from a proximal end face of the first guide coil attachment block 53. In other words, the upward guide coil 43u returns to a compression-free state.

Figure 5:
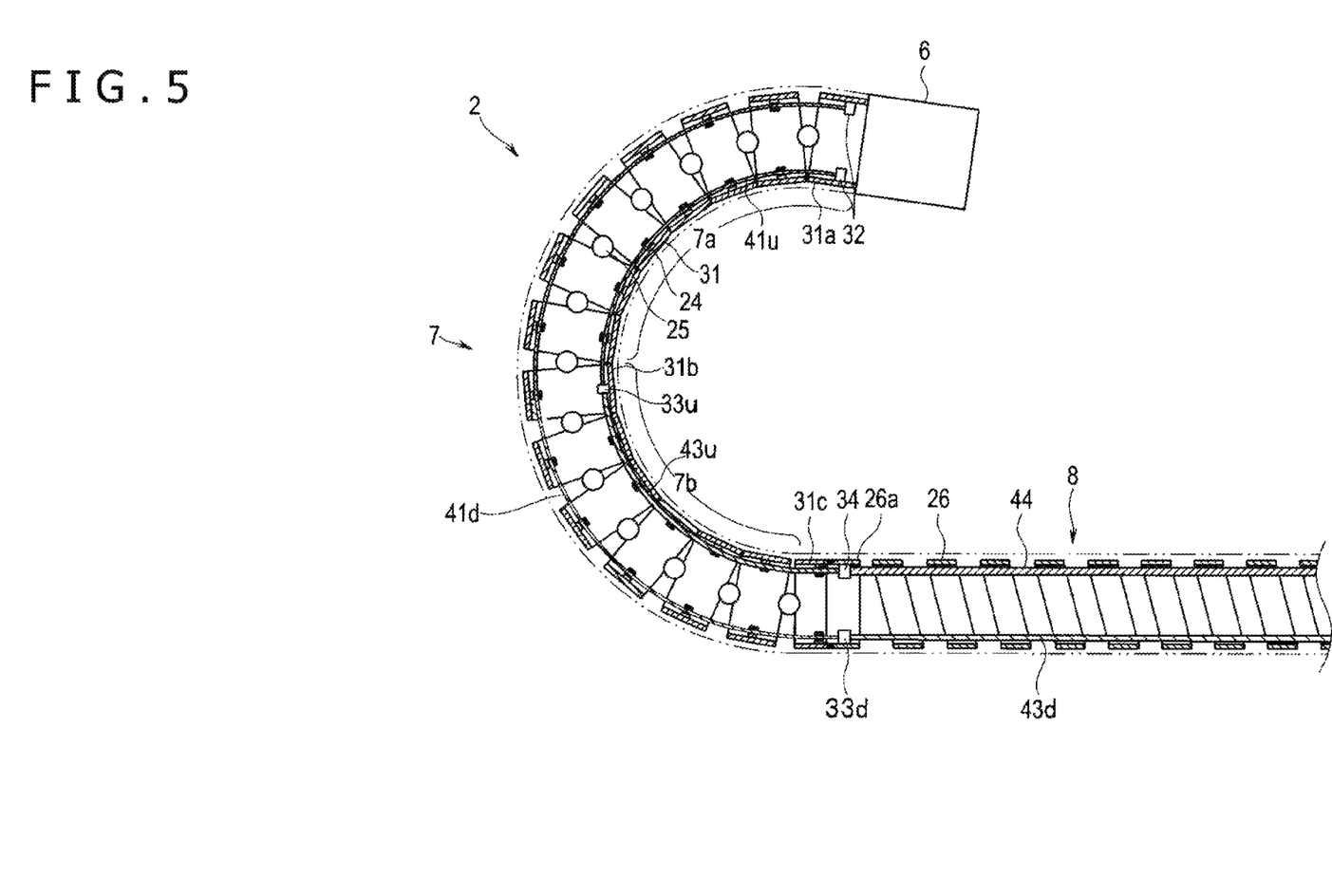
FIG. 5 is a cross-sectional view illustrating a state in which the bendable part has been bent in its entirety.
Figure 6:
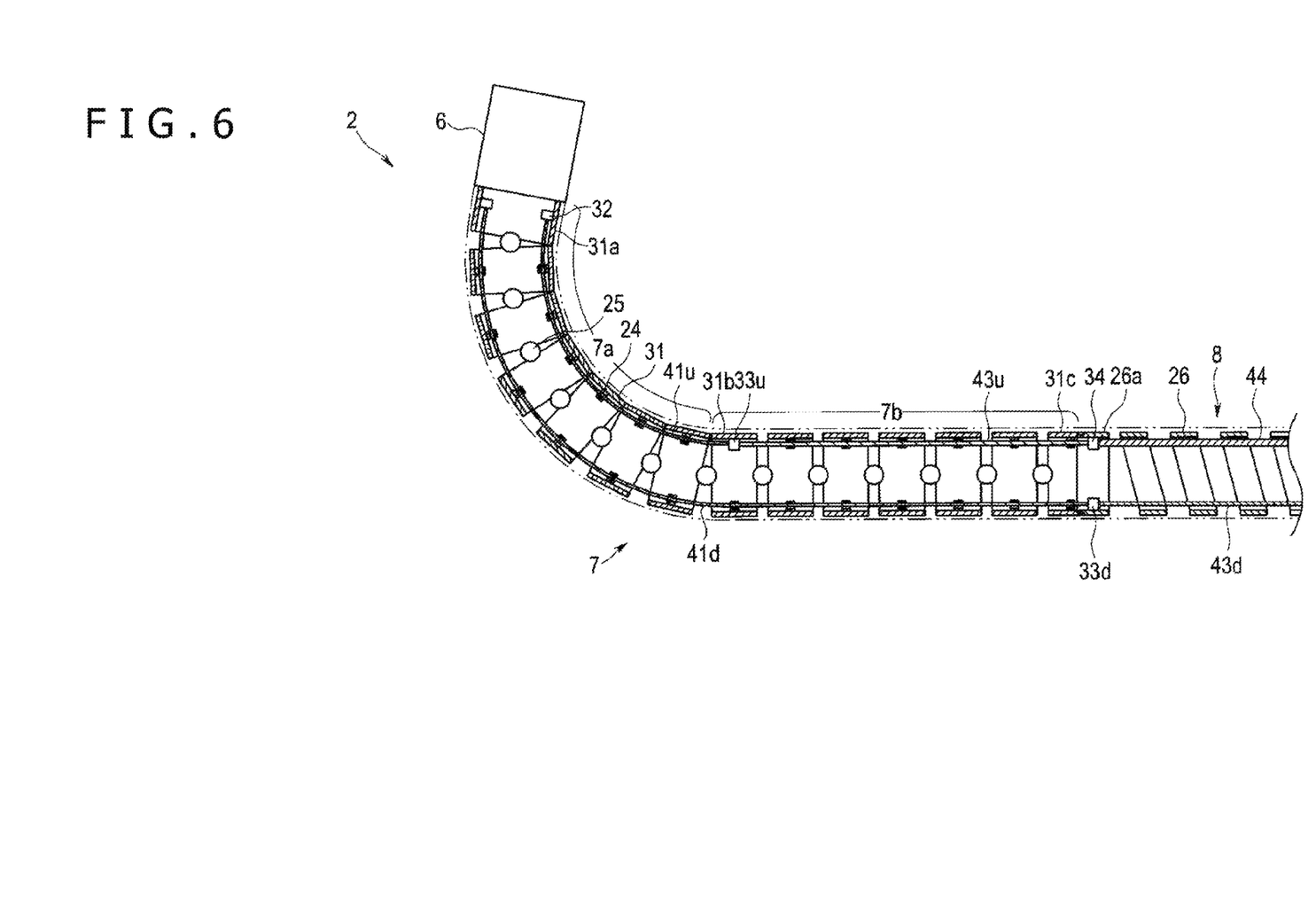
FIG. 6 is a cross-sectional view illustrating the bendable part in which only a first bendable portion has been bent.

The operation and functions of the endoscope 1 configured as described above is now described. In the endoscope 1, the bendable part 7 is in the long-length bent state when the selector lever 21 is in the initial position illustrated in FIG. 3. Now, if the user operates the bending operation lever 13 to turn it, for example, in the UP direction, the upward bending operation wire 41u is pulled so that the bendable part 7 is progressively bent in the UP direction. At this time, the second bendable portion 7b, which is located on the side of the distal end of the flexible tube part 8, and the first bendable portion 7a, which is located on the side of the distal end of the second bendable portion 7b, are bent as illustrated in FIG. 5. On the other hand, in the endoscope 1, the bendable part 7 is changed from the long-length bent state to the short-length bent state by operating the selector lever 21. At this time, the upward guide coil 43u is compressed in association with the operation of the selector lever 21 as illustrated in FIG. 4F. If the user operates the bending operation lever 13 to turn it in the UP direction in this state, the upward bending operation wire 41u is pulled so that the bendable part 7 is bent in the UP direction. At this time, only the first bendable portion 7a which is located on the side of the distal end of the bendable part 7 is bent toward an upward direction as illustrated in FIG. 6.

In other words, according to the endoscope 1 of this embodiment, the upward guide coil 43u can be gradually compressed and stiffened by operating the selector lever 21, which is disposed on the operation unit 3, to a change-over position. Therefore, the user can selectively change between two states. In one state, only the first bendable portion 7a as the distal portion of the bendable part 7 is bent in an upward direction to permit bending in a small radius. In the other state, the bendable part 7 is bent in its entirety as in the conventional way. As described hereinbefore, according to the endoscope 1 of this embodiment, it is possible to readily achieve a first state and a second state by simply operating the selector lever 21 upon bending operation of the bendable part 7. Only the first bendable portion 7a on the side of the distal end of the bendable part 7 is substantially bent in the first state. The first bendable portion 7a and second bendable portion 7b are both bent in the second state. As a consequence, upon inserting the insert section 2 of the endoscope 1 into a deep part of a complex body cavity, only the first bendable portion 7a on the side of the distal end the bendable part 7 can be bent, so that the endoscope 1 can be bent in a small radius and the insertion maneuverability into the complex body cavity is improved.

In the embodiment described hereinbefore, the description is made of the configuration that the upward guide coil 43*u* with the upward bending operation wire 41*u* inserted therein is compressed by the selection device 54. Instead of the upward guide coil 43*u* with the upward bending operation wire 41*u* inserted therein, however, it may be configured to compress the downward guide coil 43*d*, in which the downward bending operation wire 41*d* is inserted, by the selection device 54. It may also be configured to arrange two selection devices 54 and to selectively compress, by the two selection devices 54, (i) the upward guide coil 43*u* with the upward bending operation wire 41*u* inserted therein and (ii) the downward guide coil 43*d* with the downward bending operation wire 41*d* inserted therein. In this embodiment, the endoscope 1 includes the selector lever braking mechanism that allows at least the upward guide coil 43*u* to maintain the state in which the upward guide coil 43*u* is pushed in toward the distal end thereof. In other words, the selector lever 21 is configured to maintain a turned state by the selector lever braking mechanism.

Figure 7:
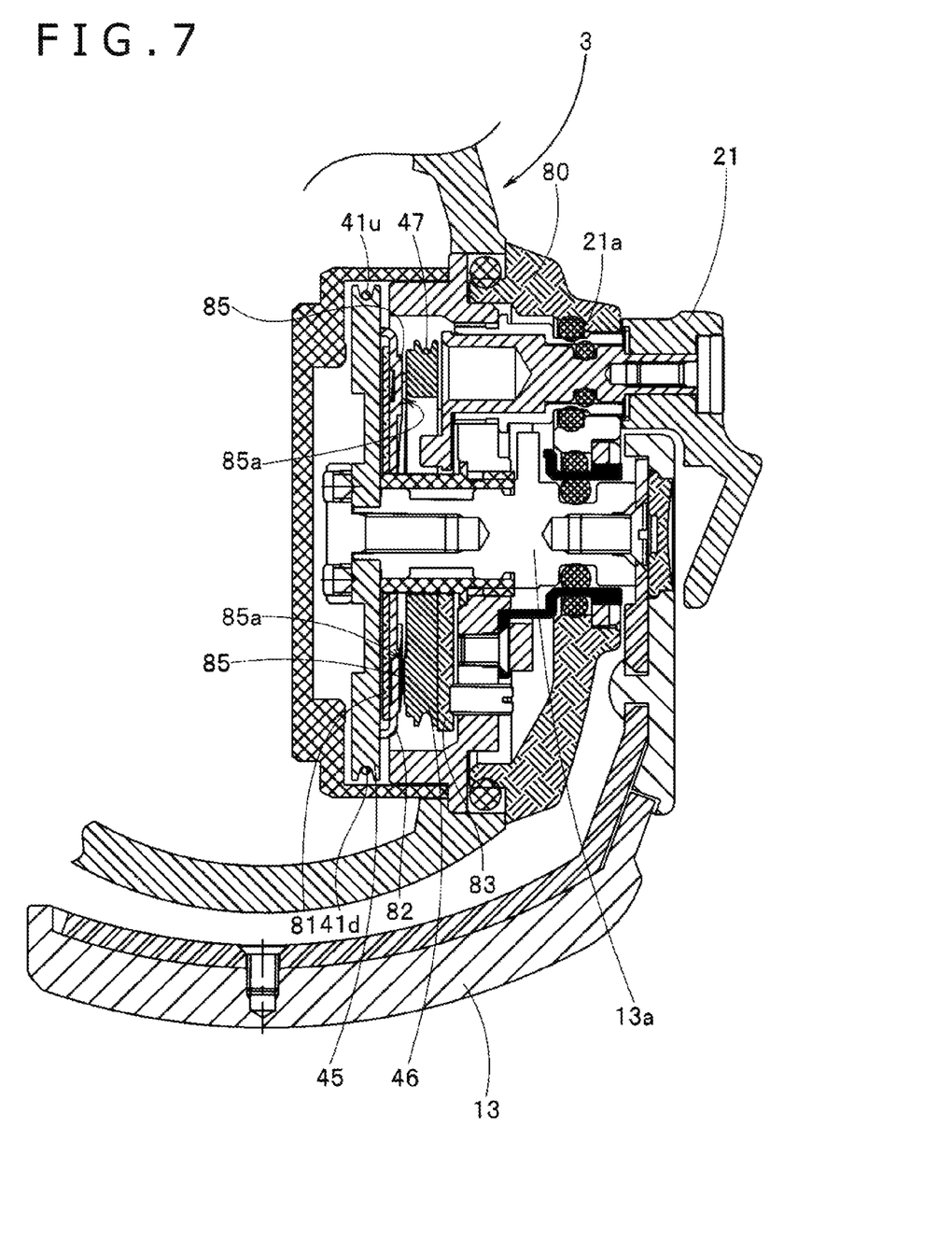
FIG. 7 is a view illustrating a relationship between a bending operation lever and a selector lever, both of which are disposed in the operation unit.
Figure 8:
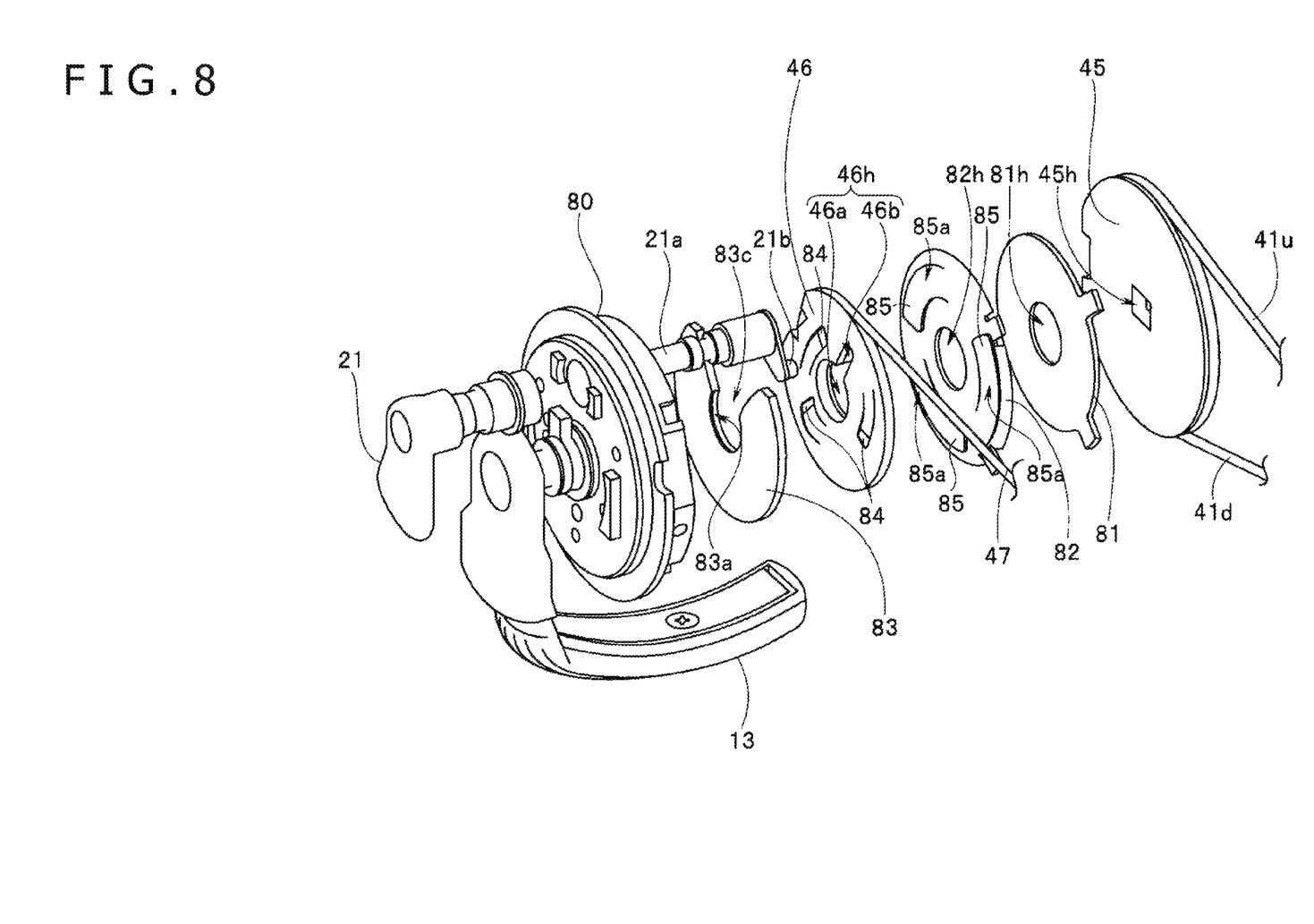
FIG. 8 is an exploded view illustrating relationships between a bending operation pulley, a friction plate, a cam plate, a bent length selection pulley and a brake plate, all of which are disposed on a bending operation lever shaft of the bending operation lever and the selector lever.

As illustrated in FIG. 7, the operation unit 3 includes the bending operation lever 13 and selector lever 21. Numeral reference 13*a* is a bending operation lever shaft, which is integrally attached on the bending operation lever 13. On the other hand, numeral reference 21*a* designates a selector lever shaft, which is integrally attached on the selector lever 21. As illustrated in FIG. 7 and FIG. 8, on the bending operation lever shaft 13*a*, the bending operation pulley 45, a friction plate 81, a cam plate 82, the bent length selection pulley 46 and a brake plate 83 all of which are disposed in this order from the side of a free end of the shaft. Numeral reference 80 designates a cover member, which is disposed on an outer surface of the operation unit 3. In this embodiment, the selector lever braking mechanism is primarily configured by the bent length selection pulley 46, friction plate 81 and cam plate 82. The cam plate 82 includes cam portions 85 as first raised portions. The cam plate 82 is disposed slidably side by side with the bent length selection pulley 46. The brake plate 83 is formed by including a notch 83*c* in a disk. The disk is made of a resin having good slidability, for example, such as polyacetal and has a predetermined thickness dimension. The notch 83*c* includes a bending operation lever bearing recess 83*a*. The bending operation lever shaft 13*a*, not illustrated in FIG. 8, is kept in engagement with the bending operation lever bearing recess 83*a*. Therefore, the brake plate 83 is disposed slidably with the bending operation lever shaft 13*a*.

The bent length selection pulley 46 is a metal-made disk, and has cam portions that are used as the braking mechanism. Designated at numeral reference 84 are "pressed depressions", which are disposed as many as three at equal intervals to form cam portions as second raised portions. Accordingly, on a side opposite to the side having the three pressed depressions 84, three "sloping raised portions" are arranged as unillustrated cam portions. These three sloping raised portions are aligned along a circumferential direction at positions of equal distance from a center of the bent length selection pulley 46. It is to be noted that when such cam portions are disposed on the bent length selection pulley 46, cam portions, for example, may be disposed on the opposite side without forming the above-mentioned pressed depressions by pressing. The bent length selection pulley 46 includes an odd-shaped hole 46*h*. The odd-shaped hole 46*h* includes an insertion hole 46*a* and an engagement slot 46*b*. In the insertion hole 46*a*, the bending operation lever shaft

13*a* is inserted. A connection protrusion 21*b* is arranged on a free end portion of the selector lever shaft 21*a* and is disposed in engagement with the engagement slot 46*b*. The engagement slot 46*b* is formed such that it outwardly extends from a circular inner peripheral wall of the substantially circular insertion hole 46*a*.

In this embodiment, the bending operation lever shaft 13*a* is inserted in the insertion hole 46*a*. As a consequence, the bent length selection pulley 46 is disposed slidably with the bending operation lever shaft 13*a*. The connection protrusion 21*b* is turned clockwise or counterclockwise in association with turning of the selector lever shaft 21*a*. Then, the bent length selection pulley 46 is rotated relative to and about the bending operation lever shaft 13*a*. The cam plate 82 is a plate member, for example, a metal-made disk, and includes the three cam portions 85 as the first raised portions. The three cam portions 85 are aligned in a circumferential direction at positions of equal distance from a center of the cam plate 82. The three cam portions 85 are located substantially opposite the cam portions of the bent length selection pulley 46. The cam portions of the bent length selection pulley 46 and the three cam portions 85 of the cam plate 82 are each a sloping raised portion having a sloping surface 85*a*. The sloping surface 85*a* is formed such that its height from the surface increases smoothly and gently along the circumferential direction. The bent length selection pulley 46 or cam plate 82 rotates in the circumferential direction. Further, each cam top is formed, for example, as a flat surface. It is to be noted that each cam top is not limited to such a flat surface but may be a curved surface.

The three cam portions 85 of the cam plate 82 are formed such that the height of the raised portion as each cam portion 85 gradually increases toward the direction in which the bent length selection pulley 46 rotates when the bent length selection wire 47 is pulled. Cam tops are arranged on the surface of the bent length selection pulley 46. On the other hand, the cam portions of the bent length selection pulley 46 are formed such that the height of the raised portion as each cam portion gradually increases toward the direction in which the bent length selection pulley 46 rotates when the bent length selection wire 47 is pulled. The cam plate 82 includes a "bending operation lever shaft bearing bore" 82*h*. The bending operation lever shaft 13*a* is inserted in the bending operation lever shaft bearing bore 82*h*. The cam plate 82 is disposed slidably with the bending operation lever shaft 13*a*. The friction plate 81 is a flat disk and made, for example, of a resin such as polyether ether ketone, or PEEK. The friction plate 81 includes a bending operation lever bearing bore 81*h*. In the bending operation lever bearing bore 81*h*, the bending operation lever shaft 13*a* is inserted. The friction plate 81 is disposed slidably with the bending operation lever shaft 13*a*. The bending operation pulley 45 includes a fixing bore 45*h*. The fixing bore 45*h* is, for example, a square-shaped through-bore. The bending operation lever shaft 13*a* is fitted and disposed and, for example, bonded and attached at a free end portion thereof in the fixing bore 45*h*. As a consequence, the bending operation lever shaft 13*a* integrally turns in association with operation of the bending operation lever 13, whereby the bent length selection pulley 46 is rotated clockwise or counterclockwise.

Now, a description will be made of operation and functions of the selector lever braking mechanism. The connection protrusion 21*b* of the selector lever 21 is disposed in the engagement slot 46*b*. Therefore, if the user operates the selector lever 21, the bent length selection pulley 46 is progressively rotated relative to the bending operation lever shaft 13a in association with the turning of the selector lever shaft 21a.

At this time, the sloping surfaces 84a of the unillustrated cam portions are disposed on the bent length selection pulley 46. The sloping surfaces 84a are arranged on the sloping surfaces 85a of the cam portions 85 disposed on the cam plate 82. Subsequently, the bent length selection pulley 46 further rotates by operation of the selector lever 21. Based on the rotation of the bent length selection pulley 46, the sloping surfaces 85a of the cam portions of the bent length selection pulley 46 progressively move on the sloping surfaces 85a of the cam portions 85 of the cam plate 82. A friction force between (i) the sloping surfaces 84a of the cam portions of the bent length selection pulley 46 and (ii) the sloping surfaces 85a of the cam portions 85 disposed on the cam plate 82 then increases gradually. By the user's operation of the selector lever 21 to the change-over position, the friction force between the cam portions of the bent length selection pulley 46 and the cam portions 85 of the cam plate 82 reaches a preset force quantity so that the selector lever 21 is attached.

As a consequence, the upward guide coil 43u with the upward bending operation wire 41u inserted therein can be maintained in a compressed state. In other words, the bendable part 7 is attached in the short-length bent state. If the selector lever 21 is returned from the change-over position to the initial state, the bent length selection wire 47 is relaxed. The pipe 69 receives an expanded force from the upward guide coil 43u which is compressed. The pipe 69 is returned to the state that the pipe 69 extends from the proximal end face of the first guide coil attachment block 53. In other words, the upward guide coil 43u returns to the compression-free state, and the bendable part 7 comes into the long-length bent state. As has been described above, the selector lever braking mechanism is provided to maintain the first guide coil in the compressed state. It is, therefore, possible to stably achieve the state, in which only the first bendable portion 7a on the side of the distal end of the bendable part 7 is bent, by operating the selector lever 21 to the change-over position. As a consequence, it is possible to stably perform observation or treatment by maintaining the insert section 2 in a bent state on the side of only the distal end of the bendable part 7.

In this embodiment, (i) the cam portions 85 are disposed as the first raised portions on the cam plate 82, (ii) the cam portions as the second raised portions are disposed on the bent length selection pulley 46, and (iii) the former and latter cam portions are arranged in an opposing positional relationship. However, the cam plate 82 may include the cam portions 85 as the first raised portions, and the cam portions as the second raised portions may be omitted on the bent length selection pulley 46.

In sum, the disclosed technology is directed to an endoscope includes a bendable part having a first bendable portion and a second bendable portion formed on a distal end thereof and configured to be bendable by pulling or relaxing a bending operation wire. A flexible tube part is disposed consecutively on a proximal end of the second bendable portion. An operation unit is disposed consecutively on a proximal end of the flexible tube part.

A first guide coil includes a distal end attached on a distal end of the second bendable portion and having the bending operation wire internally inserted therethrough. A second guide coil includes a distal end and a proximal end in which the distal end of the second guide coil is attached to a distal end portion of the flexible tube and the proximal end of the second guide coil is attached in the operation unit. The first guide coil is internally inserted into second guide coil.

A movable member is disposed advanceable and retractable in the operation unit with the first guide coil being connected at a proximal end thereof to the movable member.

A selection member is configured to be moved to press the movable member and to compress the first guide coil, whereby the first guide coil is increased in stiffness to change the bendable part from a long-length bent state. The bendable part is bent over its entirety to a short-length bent state and in which the first bendable portion is bent.

A selector lever braking mechanism is configured to maintain the short-length bent state to which the bendable part is changed by pressing the movable member via the selection member.

A transmission member having a distal end that is connected to the selection member and is configured to bring the selection member into contact with the movable member so that a force is transmitted to push in the movable member.

The selector lever braking mechanism includes a rotatable member having a proximal end and is rotatably disposed in the operation unit with the transmission member being connected on the proximal end to a position of a predetermined rotation radius on the rotatable member and is configured to rotate so that the transmission member is pushed or pulled to allow the movable member to advance or to retract via the selection member. A plate member is disposed slidably side by side with the rotatable member in the operation unit and having a first raised portion formed so that a sliding friction force increases with rotation of the rotatable member.

The rotatable member includes a second raised portion formed so that a friction force with the first raised portion increases with rotation of the rotatable member. The first raised portion includes a first sloping surface with a height gradually increasing toward a direction in which the rotatable member rotates. The second raised portion includes a second sloping surface with a height gradually increasing toward a direction opposite to a direction in which the rotatable member rotates.

According to the endoscope of the present disclosure, the changing of the bendable part between the long-length bent state and the short-length bent state can maintain the short-length bent state while ensuring improved insertion maneuverability into a deep part of a complex body cavity. The present disclosure can, therefore, provide an endoscope that can perform observation or treatment with excellent operability.

The present disclosure described hereinbefore should not be limited to the above-described embodiment and modifications, and various changes, modifications and the like are feasible within a scope not altering the spirit of the present invention.

What is claimed is:
1. An endoscope comprising:
a bendable part including a first bendable portion and a second bendable portion disposed at a proximal end of the first bendable portion, the bendable part being configured to bend by pulling or releasing a bending operation wire;
a flexible tube part disposed at a proximal end of the second bendable portion;
an operation unit, including a grip and operation buttons, disposed at a proximal end of the flexible tube part;

a first guide coil having a distal end being attached to a distal end of the second bendable portion, the first guide coil including the bending operation wire internally inserted therethrough;

a second guide coil having a distal end and a proximal end, the distal end of the second guide coil being attached to a distal end portion of the flexible tube part and the proximal end of the second guide coil being attached to the operation unit and the first guide coil being inserted into second guide coil;

a guide coil receiver configured to advance and retract in the operation unit, a proximal end of the first guide coil being connected to the guide coil receiver;

pressing block configured to press the guide coil receiver and to compress the first guide coil in a direction of a distal end of the first guide coil, to increase a stiffness of the first guide coil and change the bendable part from a long-length bent state wherein the bendable part is bent over an entirety of the bendable part to a short-length bent state wherein the first bendable portion is bent less than in the long-length bent state; and a selector lever braking mechanism configured to maintain the short-length bent state by pressing the guide coil receiver in a direction in which the first guide coil is compressed in a direction of the distal end of the first guide coil.

2. The endoscope of claim 1, further comprising: a selection wire having a distal end that being connected to the pressing block and being configured to bring the pressing block into contact with the guide coil receiver so that a force is transmitted to push in the guide coil receiver.

3. The endoscope of claim 2, further comprising:

a bent length selector lever disposed in the operation unit and configured to select one of the long-length bent state and the short-length bent state, wherein:

the selector lever braking mechanism includes:

a pulley rotatably disposed in the operation unit, connected to the bent length selector lever, the selection wire being connected on the proximal end to a position of a predetermined rotation radius on the pulley, the pulley being configured to rotate together with a rotation of the bent length selector lever, and to rotate so that the selection wire is pushed or pulled to allow the guide coil receiver to advance or to retract via the pressing block; and a plate member being disposed slidably side by side with the pulley in the operation unit and having a first raised portion formed so that a sliding friction force increases with rotation of the pulley; and the short-length bent state is maintained by fixing the bent length selector lever with the sliding friction force between the plate member.

4. The endoscope of claim 3, wherein the pulley includes a second raised portion formed so that a friction force with the first raised portion increases with rotation of the pulley.

5. The endoscope of claim 3, wherein the first raised portion includes a first sloping surface with a height gradually increasing toward a direction in which the pulley rotates.

6. The endoscope of claim 4, wherein the second raised portion includes a second sloping surface with a height gradually increasing toward a direction opposite to a direction in which the pulley rotates.

7. The endoscope of claim 1, the pressing block further including a slot and a wire anchor hole.

8. The endoscope of claim 7, the pressing block further including a pin bore disposed between the slot and the wire anchor hole.

9. The endoscope of claim 8, wherein a central axis of the pin bore is orthogonal to a central axis of the slot.

* * * * *